US010578542B2

(12) United States Patent
Cao et al.

(10) Patent No.: US 10,578,542 B2
(45) Date of Patent: Mar. 3, 2020

(54) MULTI-PHOTON COUNTING FOR HIGH SENSITIVITY FLOW CYTOMETER SYSTEMS AND METHODS FOR USING THE SAME

(71) Applicant: Becton, Dickinson and Company, Franklin Lakes, NJ (US)

(72) Inventors: Jianying Cao, San Jose, CA (US); Wei Chen, San Jose, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 16/135,819

(22) Filed: Sep. 19, 2018

(65) Prior Publication Data
US 2019/0113435 A1    Apr. 18, 2019

Related U.S. Application Data

(60) Provisional application No. 62/572,949, filed on Oct. 16, 2017.

(51) Int. Cl.
*G01N 15/14* (2006.01)
*G01N 33/49* (2006.01)
*G01N 15/10* (2006.01)

(52) U.S. Cl.
CPC ..... *G01N 15/1436* (2013.01); *G01N 15/1404* (2013.01); *G01N 15/1427* (2013.01);
(Continued)

(58) Field of Classification Search
CPC ........... G01N 15/1436; G01N 15/1404; G01N 15/1459; G01N 15/1427; G01N 2015/1486; G01N 33/4915
See application file for complete search history.

(56) References Cited

U.S. PATENT DOCUMENTS

| 5,308,990 A | * | 5/1994 | Takahashi | .......... | G01N 15/1459 |
| | | | | | 250/458.1 |
| 5,891,738 A | * | 4/1999 | Soini | ................ | G01N 33/54313 |
| | | | | | 435/6.11 |

(Continued)

OTHER PUBLICATIONS

SensL, "An Introduction to the Silicon Photomultiplier", www.sensl.com, Rev. 6.0, Feb. 2017, 16 pages.
(Continued)

*Primary Examiner* — Sang H Nguyen
(74) *Attorney, Agent, or Firm* — Khin K. Chin; Bret E. Field; Bozicevic, Field & Francis LLP

(57) ABSTRACT

Aspects of the present disclosure include methods and systems for detecting light from a sample in a flow stream by multi-photon counting. Methods according to certain embodiments include irradiating a sample in a flow stream with a light source and detecting light from the sample in the flow stream and counting photons of the detected light by integrating photo-electron charge over a time interval. Methods also include irradiating a sample in a flow stream with a light source, detecting light from the sample in the flow stream and outputting a digital output signal and an analog output signal produced by the detected light. Systems for detecting light from a sample in a flow stream with a detector and counting photons by integrating photo-electron charge over a time interval are also described. Kits having a detector, a photon counter and a flow cell configured to propagate a sample in flow stream are also provided.

19 Claims, 6 Drawing Sheets

(52) U.S. Cl.
CPC ..... *G01N 15/1429* (2013.01); *G01N 15/1459* (2013.01); *G01N 33/4915* (2013.01); *G01N 2015/1006* (2013.01); *G01N 2015/1486* (2013.01)

(56) References Cited

U.S. PATENT DOCUMENTS

| | | | | |
|---|---|---|---|---|
| 6,177,277 | B1* | 1/2001 | Soini | G01N 15/1434 |
| | | | | 356/72 |
| 9,013,692 | B2* | 4/2015 | Hu | G01N 15/147 |
| | | | | 250/459.1 |
| 9,494,598 | B2* | 11/2016 | Goix | G01N 21/6428 |
| 9,575,060 | B2* | 2/2017 | Nishikawa | G02B 21/00 |
| 2002/0158212 | A1* | 10/2002 | French | B01L 3/50853 |
| | | | | 250/459.1 |
| 2004/0166514 | A1* | 8/2004 | Puskas | C12P 19/34 |
| | | | | 435/6.12 |
| 2010/0163748 | A1* | 7/2010 | Dhadwal | G01N 21/6428 |
| | | | | 250/459.1 |
| 2011/0044910 | A1* | 2/2011 | Lin | A61B 5/0059 |
| | | | | 424/9.6 |
| 2014/0374622 | A1* | 12/2014 | Cronin | G01J 1/0492 |
| | | | | 250/459.1 |
| 2015/0233820 | A1* | 8/2015 | Roke | G01N 21/47 |
| | | | | 356/338 |
| 2017/0016813 | A1* | 1/2017 | Wagner | G01N 21/3577 |

OTHER PUBLICATIONS

Keller, "Single-Molecule Fluorescence Analysis in Solution", Applied Spectroscopy, vol. 50, No. 7, 1996, 21 pages.

\* cited by examiner

MULTI-PHOTON COUNTING FOR HIGH SENSITIVITY FLOW CYTOMETER SYSTEMS AND METHODS FOR USING THE SAME

CROSS-REFERENCE TO RELATED APPLICATION

Pursuant to 35 U.S.C. § 119(e), this application claims priority to the filing date of U.S. Provisional Patent Application Ser. No. 62/572,949, filed Oct. 16, 2017; the disclosure of which application is incorporated herein by reference.

INTRODUCTION

The characterization of analytes in biological fluids has become an integral part of medical diagnoses and assessments of overall health and wellness of a patient. In particular, analyte detection in physiological fluids, e.g., blood or blood derived products, can be important where the results may play a prominent role in the treatment protocol of a patient in a variety of disease conditions.

Light detection is often used to characterize components of a sample (e.g., biological samples), for example when the sample is used in the diagnosis of a disease or medical condition. When a sample is irradiated, light can be scattered by the sample, transmitted through the sample as well as emitted by the sample (e.g., by fluorescence). Variations in the sample components, such as morphologies, absorptivity and the presence of fluorescent labels may cause variations in the light that is scattered, transmitted or emitted by the sample. These variations can be used for characterizing and identifying the presence of components in the sample. To quantify these variations, the light is collected and directed to the surface of a detector.

One technique that utilizes light detection to characterize the components in a sample is flow cytometry. Using data generated from the detected light, distributions of the components can be recorded and where desired material may be sorted. A flow cytometer typically includes a sample reservoir for receiving a fluid sample, such as a blood sample, and a sheath reservoir containing a sheath fluid. The flow cytometer transports the particles (including cells) in the fluid sample as a cell stream to a flow cell, while also directing the sheath fluid to the flow cell. Within the flow cell, a liquid sheath is formed around the cell stream to impart a substantially uniform velocity on the cell stream. The flow cell hydrodynamically focuses the cells within the stream to pass through the center of a light source in a flow cell. Light from the light source can be detected as scatter or by transmission spectroscopy or can be absorbed by one or more components in the sample and re-emitted as luminescence.

SUMMARY

Aspects of the present disclosure include methods and systems for detecting light from a sample in a flow stream by multi-photon counting. Methods according to certain embodiments include irradiating a sample in a flow stream with a light source and detecting light from the sample in the flow stream and counting photons of the detected light by integrating photo-electron charge over a time interval. Methods also include irradiating a sample in a flow stream with a light source, detecting light from the sample in the flow stream and outputting a digital output signal and an analog output signal produced by the detected light. Systems for detecting light from a sample in a flow stream with a detector and counting photons by integrating photo-electron charge over a time interval are also described. Kits having a detector, a photon counter and a flow cell configured to propagate a sample in flow stream are also provided.

In embodiments, a sample in a flow stream is irradiated with a light source. In some instances, the light source is a laser, such as a continuous wave laser or a pulsed laser. In other embodiments, the light source is a light emitting diode (LED). The light source may be a broadband light source, such as lamp or broadband LED. In other embodiments, the light source may be a narrow band light source, such as a discrete band LED or a single wavelength laser.

Light is impinged onto a sample flowing in a flow stream and light from the sample in the flow stream is detected by multi-photon counting. In some embodiments, multi-photon counting includes counting photons of the detected light by integrating photo-electron charge over a time interval, such as over a plurality of time intervals. In some embodiments, the time interval is a predetermined time interval. Where counting photons includes integrating photo-electron charge over a plurality of time intervals, each time interval may be separated by a reset period where no photons are counted (i.e., no integration of photo-electron charge from the detector). In some instances, the time intervals are the same duration. In other instances, the time intervals are a different duration. In yet other instances, two or more of the time intervals are the same duration and two or more of the time intervals are a different duration. In some embodiments, counting photons according to the subject methods includes integrating photo-electron charge with a first photon counter over a first time interval and integrating photo-electron charge with a second photon counter over a second time interval. In these embodiments, there may be at least a partial overlap between the first time interval and the second time interval. In certain instances, counting photons includes integrating photo-electron charge with a first photon counter over a plurality of time intervals, each time interval being separated by a reset period therebetween and integrating photo-electron charge with a second photon counter during each reset period of the first photon counter. In some instances, methods include integrating photo-electron charge with the first photon counter during the reset period of the second photon counter. In still other embodiments, counting photons includes integrating photo-electron charge when the light detected by the detector exceeds a predetermined threshold. In these embodiments, integration of photo-electron charge by the photon counter is stopped when the light detected by the detector falls below the predetermined threshold.

In some embodiments, multi-photon counting includes counting a plurality of pulses where each pulse is produced by a single photon impinging onto the multi-photon counting detector. The light intensity of light detected from the sample in the flow stream is, in some instances, determined by the number of counted pulses. Multi-photon counting of light from the sample in the flow stream according to certain embodiments, includes photon counting of 0.2 photons/vs or more, such as photon counting of 100 photons/vs or more.

Light from a sample in the flow stream may be detected by forward scattered light, side scattered light, transmitted light, emitted light or a combination thereof. In certain embodiments, methods include multi-photon counting of photons from side scattered light from the sample in the flow stream. Light detection may also include analog light detection. In some instances, methods include a combination of multi-photon counting and analog light detection, such as where scattered light from the sample in the flow stream is detected and photons are counted by multi-photon counting and emitted light from the sample in the flow stream is detected by analog light detection or where side scattered light from the sample in the flow stream is detected and photons are counted by multi-photon counting and forward scattered light from the sample in the flow stream is detected by analog light detection.

Methods also include outputting a signal produced by the detected light. In some embodiments, the outputted signal is a digital output signal. In other embodiments, the outputted signal is an analog output signal. In yet other embodiments, the outputted signal include both a digital output signal component and an analog output signal component. In certain embodiments, methods include simultaneously outputting a digital output signal and an analog output signal. In these embodiments, methods include irradiating a sample in a flow stream with a light source, detecting light from the sample and counting photons by multi-photon counting and analog light detection and outputting (either sequentially or simultaneously) a digital output signal and an analog output signal.

In certain embodiments, the sample in the flow stream includes cells and methods include characterizing extracellular vesicles of the cells in the flow stream. Characterizing the extracellular vesicles of the cells may include identifying the type of extracellular vesicles in the cells and/or determining the size of the extracellular vesicles in the cells. To characterize cells in the flow stream, the flow rate of the sample is, according to embodiments, a rate that is sufficient for detecting light by multi-photon counting. In some instances, the sample flow rate in the flow stream is from about 1 nL/min to about 100 nL/min. In other instances, the sample flow rate in the flow stream is from about 5 nL/min to about 6 nL/min.

Aspects of the present disclosure also include systems for detecting light from a sample in a flow stream according to the subject methods. Systems according to certain embodiments include a flow cell configured to propagate a sample in a flow stream, a light source to irradiate the sample in the flow stream and a detector to detect light from the sample in the flow stream and a photon counter that counts photons of the detected light by integrating photo-electron charge over a predetermined time interval. The light source in the subject system may be a broad-band light source, such as a broad-band lamp or LED, or may be a narrow-band light source, such as a narrow-band LED, single wavelength LED or single wavelength laser (e.g., pulsed or continuous wave laser).

Light from the sample in the flow stream is detected by a detector and counted with the multi-photon counter. In some embodiments, the photon counter is configured to count photons of the detected light by integrating photo-electron charge over a time interval, such as over a plurality of time intervals. Where counting photons includes integrating photo-electron charge over a plurality of time intervals, each time interval may be separated by a reset period where no photons are counted (i.e., no integration of photo-electron charge from the detector) by the multi-photon counter. In some instances, the time intervals are the same duration. In other instances, the time intervals are a different duration. In yet other instances, two or more of the time intervals are the same duration and two or more of the time intervals are a different duration. In some embodiments, systems include a first photon counter configured to integrate photo-electron charge over a first time interval and a second photon counter configured to integrate photo-electron charge over a second time interval. In these embodiments, there may be at least a partial overlap between the first time interval and the second time interval. In certain instances, systems include a first photon counter configured to integrate photo-electron charge over a plurality of time intervals, each time interval being separated by a reset period therebetween and a second photon counter configured to integrate photo-electron charge during each reset period of the first photon counter. In some instances, the first photon counter is configured to integrate photo-electron charge during the reset period of the second photon counter. In still other embodiments, systems of interest include a photon counter configured to integrate photo-electron charge when the light detected by the detector exceeds a predetermined threshold. In these embodiments, the photon counter is configured to stop integrating photo-electron charge counter when the light detected by the detector falls below the predetermined threshold.

In some embodiments, the multi-photon counter is configured to count pulses where each pulse is produced by a single photon impinging on an active surface of the detector. The intensity of light detected by the detector may in certain instances be determined by the number of counted pulses. Multi-photon counters are, in certain embodiments, configured to count 0.2 photons/vs or more, such as photon counting of 100 photons/vs or more from light from the flow stream.

In some instances, the multi-photon counting detector is a detector array composed of a plurality of detectors. Among the plurality of detectors may be one or more solid-state detectors, such as avalanche photodiodes. In certain instances, the detector array is composed of a plurality of solid state detectors, such as an array of avalanche photodiodes. Detector arrays may include 10 or more detectors, such as 100 or more detectors. In certain embodiments, the multi-photon counting detector is a silicon photomultiplier. Multi-photon counting detectors may be positioned to detect forward scattered light, side scattered light, transmitted light, emitted light or a combination thereof from the sample in the flow stream. Light from the sample in the flow stream may be detected and characterized by photon counting and analog light detection. In certain embodiments, light from the sample in the flow stream is concurrently detected and characterized by photon counting and analog light detection.

The multi-photon counting detector is configured to output a signal produced by the detected light. In some embodiments, the multi-photon counting detector is configured to output a digital output signal. In other embodiments, the multi-photon counting detector is configured to output an analog output signal. In yet other embodiments, the multi-photon counting detector is configured to output a digital output signal and an analog output signal. In still other embodiments, the multi-photon counting detector is configured to simultaneously output a digital output signal and an analog output signal.

The output signal from the detected light is used to characterize sample components in the flow stream. In embodiments, the flow rate of the flow stream is a rate that is sufficient to detect light from particles in the flow stream by multi-photon counting, such as a rate of from about 1 nL/min to about 100 nL/min, such as from about 5 nL/min to about 6 nL/min. In some embodiments, systems further include a pump in fluid communication with the flow cell for controlling the flow rate of sample in the flow stream. For example, systems may include a peristaltic pump or a peristaltic pump with a pulse damper.

Kits including one or more components of the subject multi-photon counting flow systems are also provided. Kits according to certain embodiments include a flow cell configured to propagate a sample in a flow stream, a detector, a photon counter that counts photons of the detected light by integrating photo-electron charge over a period of time and an optical adjustment component. Optical adjustment components may be, for example, a focusing lens, a collimator, beam splitter, a wavelength separator or a combination thereof. Kits may also include optical relay systems for propagating light from the sample in the flow stream to the multi-photon counting detector, such as a free-space light relay system or fiber optics (e.g., a fiber optics light relay bundle). Kits may also include a pump for controlling the rate of the flow stream for multi-photon counting of light from sample, such as a peristaltic pump or a peristaltic pump with a pulse damper.

BRIEF DESCRIPTION OF THE FIGURES

The invention may be best understood from the following detailed description when read in conjunction with the accompanying drawings. Included in the drawings are the following figures.

DETAILED DESCRIPTION

Figure 1:
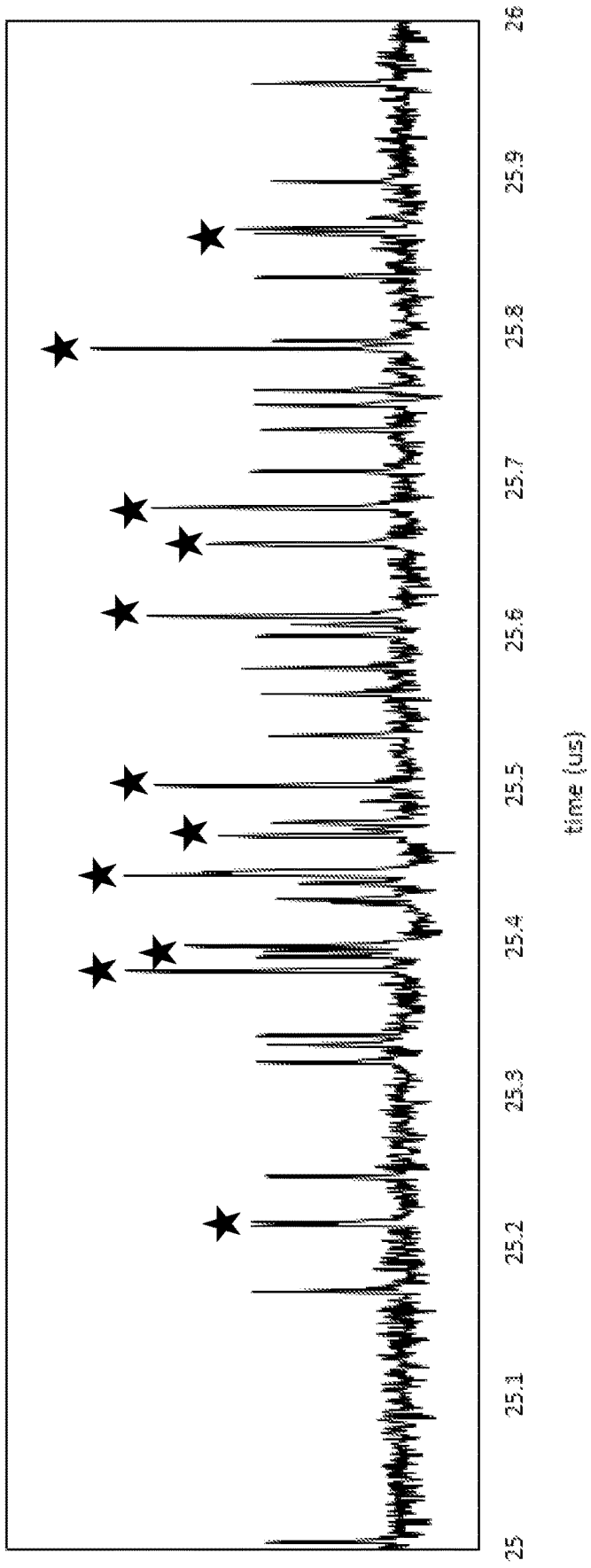
FIG. 1 depicts a sample output waveform from light detected by a multi-photon detector according to certain embodiments of the present disclosure.

Aspects of the present disclosure include methods and systems for detecting light from a sample in a flow stream by multi-photon counting. Methods according to certain embodiments include irradiating a sample in a flow stream with a light source and detecting light from the sample in the flow stream and counting photons of the detected light by integrating photo-electron charge over a predetermined time interval. Methods also include irradiating a sample in a flow stream with a light source, detecting light from the sample in the flow stream and outputting a digital output signal and an analog output signal produced by the detected light. Systems for detecting light from a sample in a flow stream with a detector and counting photons by integrating photo-electron charge over a predetermined time interval are also described. Kits having a detector, a photon counter and a flow cell configured to propagate a sample in flow stream are also provided.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides methods for detecting light from a sample in a flow stream by multi-photon counting. In further describing embodiments of the disclosure, methods for detecting particles (e.g., cells and extracellular vesicles) in a sample in a flow stream are first described in greater detail. Next, systems having a multi-photon counting detector configured for detecting light and counting photons from a sample in a flow stream are described. Kits having a flow cell and one or more multi-photon counting detectors along with a photon counter configured to integrate photo-electron charge and an optical adjustment component are also provided.

Methods for Measuring Light from a Sample in a Flow Stream by Multi-Photon Counting Aspects of the disclosure include methods for measuring light from a sample in a flow stream (e.g., in a flow cytometer) by multi-photon counting. In practicing methods according to embodiments, a sample is irradiated with a light source, light from the sample in the flow stream is detected with a multi-photon counting detector and photons are counted by integrating photo-electron charge over a predetermined time interval. The term "multi-photon counting" is used herein in its conventional sense to refer to the detection and counting of a plurality of individual photons with a detector, such as a photomultiplier or photon avalanche diode (as described in greater detail below). Multi-photon counting according to certain embodiments includes receiving a waveform output from the detector and integrating photo-electron charge over a predetermined time interval. In other embodiments, multi-photon counting includes counting pulses (e.g., electronic pulses) generated by photons impinging onto the active surface of the detector. The number of photons counted (based on the number of electronic pulses generated), in some instances, is representative of the intensity of light from the sample in the flow stream. In some embodiments, multi-photon counting of detected light from the sample in the flow stream according to the subject methods is sufficient to broaden the range of intensity detection and quantitation as compared to single photon counting by 2 fold or greater, such as by 3 fold or greater, such as by 5 fold or greater, such as by 10 fold or greater, such as by 25 fold or greater, such as by 50 fold or greater and including by 100 fold or greater.

As described in greater detail below, multi-photon counting of light from a sample in a flow stream may include detection of the light by a detector (or detector array) that includes a photomultiplier, an avalanche photodiode, a detector array composed of a plurality of photodiodes or a combination thereof. FIG. 1 depicts a sample output waveform from light detected by a multi-photon detector (e.g., a silicon photomultiplier (SiPM)) according to certain embodiments of the present disclosure. Each peak in the waveform corresponds to photons impinging onto the detector surface. The marked peaks in FIG. 1 result from more than one photon but would be counted as a single photon by standard photon counting protocols.

In some embodiments, multi-photon counting includes detecting light from the sample in the flow stream and counting photons of the detected light by integrating photo-electron charge over a time interval. Time intervals according to the subject methods may be a duration that varies and may be 100 µs or less, such as 90 µs or less, such as 80 µs or less, such as 70 µs or less, such as 60 µs or less, such as 50 µs or less, such as 40 µs or less, such as 30 µs or less, such as 20 µs or less, such as 10 µs or less, such as 5 µs or less, such as 1 µs or less, such as 0.5 µs or less, such as 0.1 µs or less, such as 0.05 µs or less, such as 0.01 µs or less, such as 0.005 µs or less and including 0.001 µs or less. In some instances, time intervals for integrating photo-electron charge to count photons detected by the detector range from 0.001 µs to 100 µs, such as from 0.005 µs to 90 µs, such as from 0.01 µs to 80 µs, such as from 0.05 µs to 70 µs, such as from 0.1 µs to 60 µs and including from 0.5 µs to 50 µs. In certain embodiments, the time intervals are predetermined time intervals.

In some instances, counting photons of the detected light includes integrating photo-electron charge over a plurality of time intervals, such as over 2 time intervals or more, such as over 3 time intervals or more, such as over 4 time intervals or more, such as over 5 time intervals or more, such as over 10 time intervals or more, such as over 15 time intervals or more and including over 25 time intervals or more. Each of the plurality of time intervals for integrating photo-electron charge may independently be the same duration or a different duration. In some embodiments, two or more of the time intervals are the same duration and two or more time intervals are different durations.

Where counting photons includes integrating photo-electron charge over a plurality of time intervals, each time interval may be separated by a reset period where no photons are counted (i.e., no integration of photo-electron charge from the detector). The reset period may be any duration, depending on the type of multi-photon counting detector (as described in greater detail below) and may be 0.0001 µs or more, such as 0.0005 µs or more, such as 0.001 µs or more, such as 0.005 µs or more, such as 0.01 µs or more, such as 0.05 µs or more, such as 0.1 µs or more, such as 0.5 µs or more, such as 1 µs or more, such as 2 µs or more, such as 3 µs or more, such as 5 µs or more, such as 10 µs or more, such as 25 µs or more, such as 50 µs or more, such as 100 µs or more, such as 250 µs or more, such as 500 µs or more and including a reset period of 1000 µs or more. For example, the duration of each reset period may independently range from 0.0001 µs to 1000 µs, such as from 0.001 µs to 750 µs, such as from 0.01 µs to 500 µs and including from 0.1 µs to 100 µs. Each reset period may be the same duration or a different duration. In some embodiments, two or more reset periods are the same duration and two or more reset periods are different durations.

Figure 2:
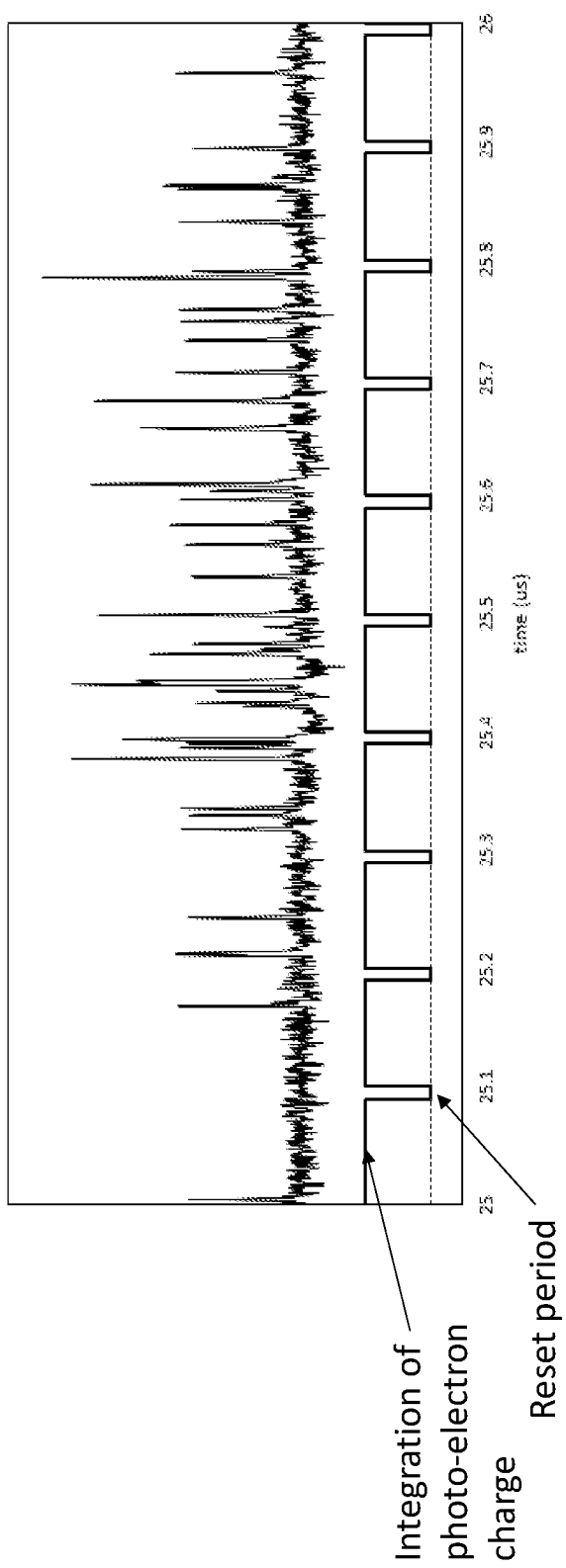
FIG. 2 depicts photon counting of detected light according to certain embodiments.
Figure 5:
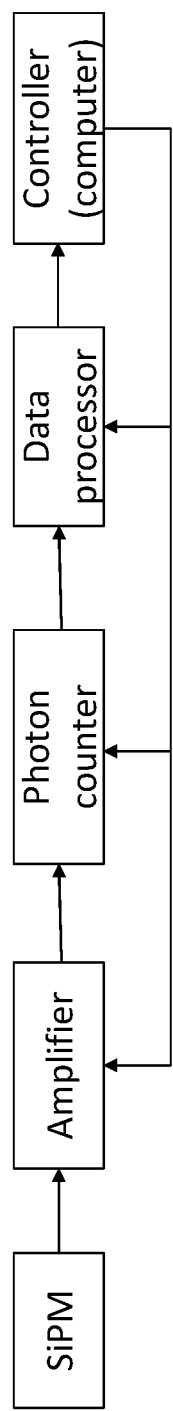
FIG. 5 depicts a schematic of a detector setup having a one photon counter according to certain embodiments.

FIG. 2 depicts photon counting of detected light according to certain embodiments. The multi-photon counter integrates the photo-electron charge for a series of time intervals (e.g., 10 time intervals) of about 0.1 µs followed by a reset period between each integration interval where photo-electron charge is not integrated. The integrated photo-electron charge is processed and an output signal is outputted to a user (FIG. 5)

In some embodiments, counting photons include integrating photo-electron charge with a first photon counter over a first time interval and integrating photo-electron charge with a second photon counter over a second time interval. In some instances, the first time interval and the second time interval partially overlap, such as overlapping for 0.0001 µs or more, such as 0.0005 µs or more, such as 0.001 µs or more, such as 0.005 µs or more, such as 0.01 µs or more, such as 0.05 µs or more, such as 0.1 µs or more, such as 0.5 µs or more including overlapping for 1 µs or more. In certain embodiments, methods including integrating photo-electron charge with a first photon counter over a plurality of time intervals, each time interval being separated by a reset period and integrating photo-electron charge with a second photon counter during each reset period of the first photon counter. In some instances, methods include integrating photo-electron charge with the first photon counter during the reset period of the second photon counter. In these embodiments, the time interval for integration of photo-electron charge from the detected light by the second photon counter may overlap the time intervals of integration by the first photon counter, such as by 0.0001 µs or more, such as by 0.0005 µs or more, such as by 0.001 µs or more, such as by 0.005 µs or more, such as by 0.01 µs or more, such as by 0.05 µs or more, such as by 0.1 µs or more, such as by 0.5 µs or more including overlapping by 1 µs or more.

Figure 3:
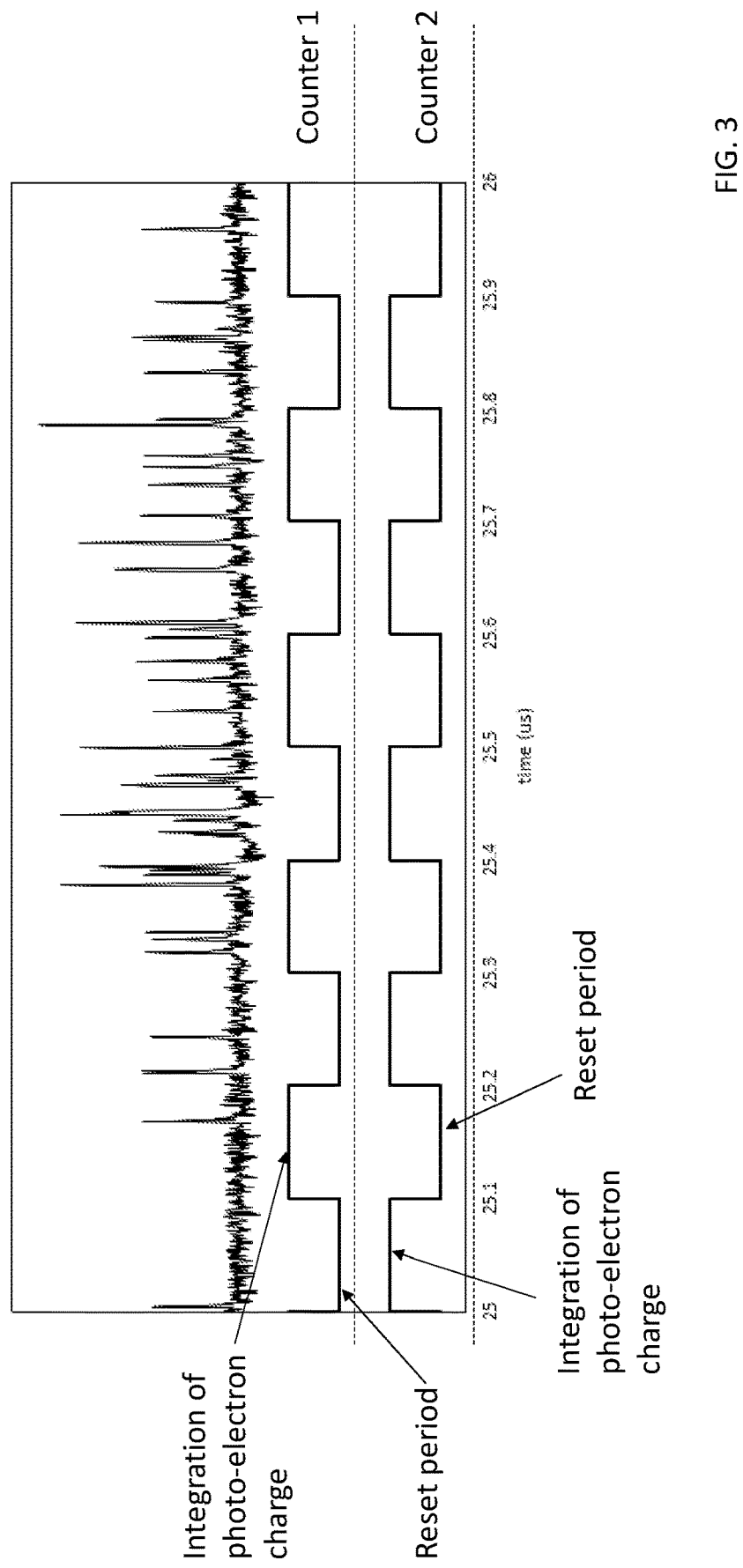
FIG. 3 depicts photon counting of detected light with two photon counters according to certain embodiments.

FIG. 3 depicts photon counting of detected light according to certain embodiments. Two photon counters are configured to integrate photo-electron charge from the detected light in tandem where the second photon counter is configured to integrate photo-electron charge during the reset period of the first photon counter and the first photon counter is configured to integrate photo-electron charge during the reset period of the second photon counter. As shown in FIG. 3, the reset period and time intervals for integration are equivalent in duration (e.g., each being 1 µs)

In certain embodiments, methods include counting photons by integrating photo-electron charge when the detected light exceeds a predetermined threshold. For example, the subject systems may be configured to integrate photo-electron charge when the signal-to-noise ratio of the outputted waveform is 2:1 or more, such as a signal-to-noise ratio of 2.5:1, such as 3:1, such as 4:1, such as 5:1, such as 10:1 and including integrating photo-electron charge when the signal-to-noise ratio is 25:1. In embodiments, integration of the photo-electron charge is stopped when the detected light falls below the predetermined threshold. In these embodiments, the time interval of integration is dynamic and will vary depending on the amount of light detected by the detector and may be 100 µs or less, such as 90 µs or less, such as 80 µs or less, such as 70 µs or less, such as 60 µs or less, such as 50 µs or less, such as 40 µs or less, such as 30 µs or less, such as 20 µs or less, such as 10 µs or less, such as 5 µs or less, such as 1 µs or less, such as 0.5 µs or less, such as 0.1 µs or less, such as 0.05 µs or less, such as 0.01 µs or less, such as 0.005 µs or less and including 0.001 µs or less. No predetermined time interval is employed and the duration of integration of the photo-electron charge depends on the intensity of the signal from the detector.

Figure 4:
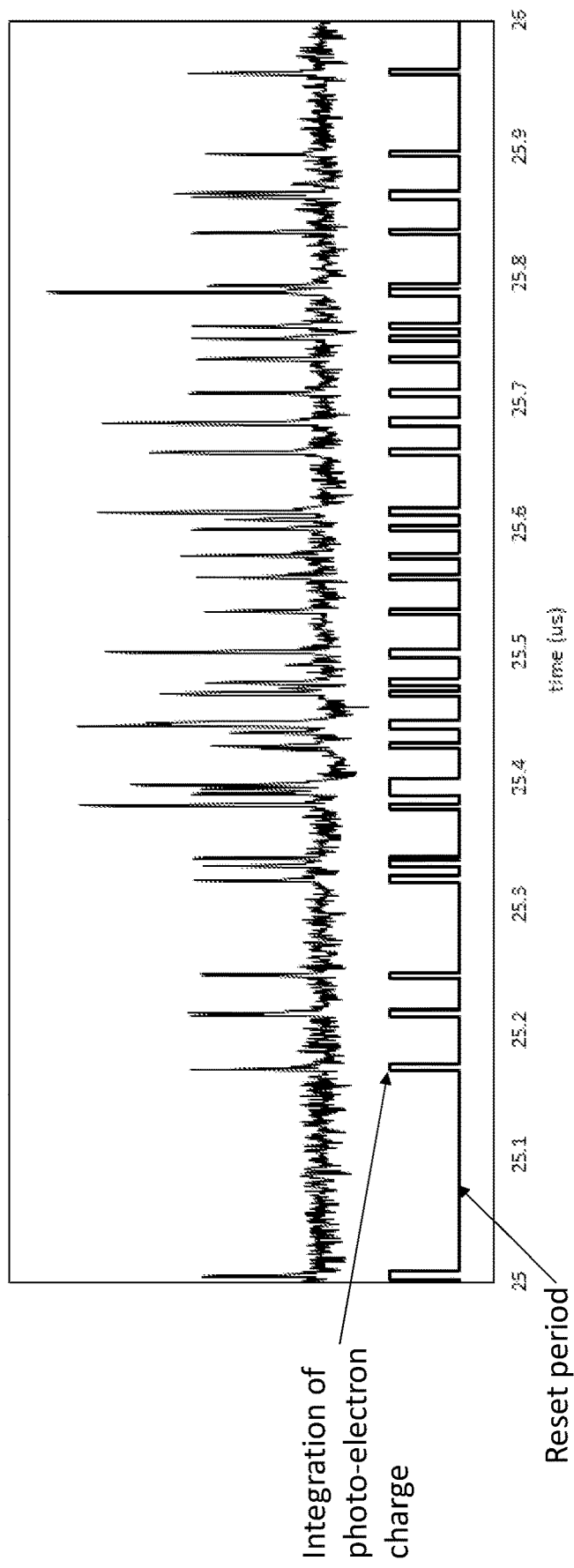
FIG. 4 depicts photon counting of detected light according to certain embodiments.

FIG. 4 depicts photon counting of detected light according to certain embodiments. The photon counter integrates photo-electron charge in response to the detected light exceeding a threshold. Where the depicted waveform exhibits a peak in light intensity, integration by the photon counter is triggered and photo-electron charge is integrated for a time interval as long as the threshold is exceeded. When the threshold is no longer exceeded, photo-electron charge integration by the photon counter is stopped and may enter a reset period. The photon counter is triggered for integration once the threshold is once again exceed. No integration time interval or reset period duration is predetermined and depends only on the detected light exceeding the predetermined threshold.

In other embodiments, multi-photon counting includes the counting of photons by generating a photoelectron pulse and counting the number of pulses generated to determine the intensity of light from the sample in the flow stream. In these embodiments, each photon impinging onto a detector active surface generates a pulse. Depending on the size of the active surface of each detector and the number of detectors (e.g., in a photodetector array), the count rate of pulses generated may be 0.1 pulse counts per µsecond or more, such as 0.2 pulse counts per µsecond or more, such as 0.3 pulse counts per µsecond or more, such as 0.5 pulse counts per µsecond or more, such as 1 pulse count per µsecond or more, such as 2 pulse counts per µsecond or more, such as 3 pulse counts per µsecond or more, such as 5 pulse counts per µsecond or more, such as 10 pulse counts per µsecond or more, such as pulse counts per µsecond or more, such as 25 pulse counts per µsecond or more, such as 50 pulse counts per µsecond or more, such as 75 pulse counts per µsecond or more, such as 100 pulse counts per µsecond or more, such as 250 pulse counts per µsecond or more, such as 500 pulse counts per µsecond or more, such as 750 pulse counts per µsecond or more, such as 1000 pulse counts per µsecond or more and including 5000 pulse counts per µsecond or more. Accordingly, the count rate of multi-photon counting according to the subject methods may be 0.1 photon counts per µsecond or more, such as 0.2 photon counts per µsecond or more, such as 0.5 photon counts per µsecond or more, such as 1 photon count per µsecond or more, such as 2 photon counts per µsecond or more, such as 3 photon counts per µsecond or more, such as 5 photon counts per µsecond or more, such as 10 photon counts per µsecond or more, such as 25 photon counts per µsecond or more, such as 50 photon counts per µsecond or more, such as 75 photon counts per µsecond or more, such as 100 photon counts per µsecond or more, such as 250 photon counts per µsecond or more, such as 500 photon counts per µsecond or more, such as 750 photon counts per µsecond or more, such as 1000 photon counts per µsecond or more and including 5000 photon counts per µsecond or more.

As described in greater detail below, the subject multi-photon counting detectors may be composed of a plurality of photodetectors, such as an array of avalanche photodiodes. Multi-photon counting of light from a sample in a flow stream according to the subject methods is, in certain embodiments, characterized by high quantum efficiency, such as a quantum efficiency of 50% or more, such as 55% or more, such as 60% or more, such as 65% or more, such as 70% or more, such as 75% or more, such as 80% or more, such as 85% or more, such as 90% or more and including a quantum efficiency of 95% or more. In other embodiments, multi-photon counting of light from a sample in a flow stream according to the subject methods is characterized by a low dark count rate, such as a dark count rate of 100 counts per second or less, such as 90 counts per second or less, such as 75 counts per second or less, such as 50 counts per second or less, such as 40 counts per second or less, such as 30 counts per second or less, such as 25 counts per second or less, such as 20 counts per second or less, such as 15 counts per second or less, such as 10 counts per second or less, such as 5 counts per second or less, such as 4 counts per second or less, such as 3 counts per second or less, such as 2 counts per second or less and including a dark count rate of 1 count per second or less.

Detected light from the sample in the flow stream may be forward scattered light, side scattered light, transmitted light, emitted light (e.g., fluorescence or phosphorescence) or a combination thereof. In some embodiments, methods include multi-photon counting of forward scattered light from the sample in the flow stream. In other embodiments, methods include multi-photon counting of side scattered light from the sample in the flow stream. In yet other embodiments, methods include multi-photon counting of light transmitted through the flow stream. In still other embodiments, methods include multi-photon counting of emitted light (e.g., fluorescence or phosphorescence) from the sample in the flow stream.

In embodiments, multi-photon counting detection systems (as described below) output a signal in response to the detected light. In certain embodiments, the output signal is a digital output signal. In other embodiments, the output signal is an analog output signal. In some instances, methods include outputting a digital output signal in response to the detected light (e.g., light detected by multi-photon counting). In other instances, methods include outputting an analog output signal in response to the detected light. In still other instances, methods include outputting a digital output signal and an analog output signal in response to the detected light. In yet other instances, methods include simultaneously outputting a digital output signal and an analog output signal in response to the detected light.

In certain embodiments, methods include multi-photon counting of light from the sample in the flow stream to produce a digital output signal in combination with analog light detection to produce an analog output signal. Depending on the intensity of light from the sample in the flow stream, the subject methods may be configured for outputting a digital output signal (by multi-photon counting) when light intensity is low (e.g., low number of generated pulses) and outputting an analog output signal when light intensity from the sample in the flow stream is high. In some instances, one or more of side scattered light, forward scattered light, and emitted light is detected by both multi-photon counting to produce a digital output signal and by analog light detection to produce an analog output signal for the detected side scattered light, forward scattered light, emitted light or combination thereof. In one example, side scattered light from the sample in the flow stream is detected by multi-photon counting to produce a digital output signal and emitted light or forward scattered light from the sample in the flow stream is detected by analog light detection to produce an analog output signal. In another example, one or more of side scattered light and forward scattered light from the sample in the flow stream is detected by multi-photon counting to produce a digital output signal and emitted light is detected by analog light detection to produce an analog output signal.

In some embodiments, light (e.g., forward scattered light, side scattered light, emitted light, etc.) is detected directly from the sample in the flow stream. In other embodiments, light from the sample in the flow stream is propagated to a detector (e.g., multi-photon counting detector) with one or more optical adjustment components. By "optical adjustment" is meant that light from the sample in the flow stream is changed as desired. For example, the beam path, direction, focus or collimation of the light from the sample in the flow stream may be changed with an optical adjustment component. In some instances, the dimensions of the light collected from the sample in the flow stream is adjusted, such as increasing the dimensions by 5% or more, such as by 10% or more, such as by 25% or more, such as by 50% or more and including increasing the dimensions by 75% or more or focusing the light so as to reduce the light dimensions, such as by 5% or greater, such as by 10% or greater, such as by 25% or greater, such as by 50% or greater and including reducing the dimensions by 75% or greater. In other instances, optical adjustment includes collimating the light. The term "collimate" is used in its conventional sense to refer to the optically adjusting the collinearity of light propagation or reducing divergence by the light of from a common axis of propagation. In some instances, collimating includes narrowing the spatial cross section of a light beam. In certain embodiments, the optical adjustment component is a wavelength separator. The term "wavelength separator" is used herein in its conventional sense to refer to an optical protocol for separating polychromatic light into its component wavelengths. Wavelength separation, according to certain embodiments, may include selectively passing or blocking specific wavelengths or wavelength ranges of the polychromatic light. Wavelength separation protocols of interest include, but are not limited to, colored glass, bandpass filters, interference filters, dichroic mirrors, diffraction gratings, monochromators and combinations thereof, among other wavelength separating protocols. In some embodiments, the wavelength separator is an optical filter. For example, the optical filter may be a bandpass filter having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm.

In certain embodiments, the detector is positioned apart in space from the sample in the flow stream and light from the sample in the flow stream is propagated to the detector through an optical relay system, such as with fiber optics or a free space light relay system. For example, the optical relay system may be a fiber optics light relay bundle and light is conveyed through the fiber optics light relay bundle to the multi-photon counting detector. Any fiber optics light relay system may be employed to propagate light to the multi-photon counting detector. In certain embodiments, suitable fiber optics light relay systems for propagating light to the multi-photon counting detector include, but are not limited to, fiber optics light relay systems such as those described in U.S. Pat. No. 6,809,804, the disclosure of which is herein incorporated by reference. In other embodiments, the optical relay system is a free-space light relay system. The phrase "free-space light relay" is used herein in its conventional sense to refer to light propagation that employs a configuration of one or more optical components to direct light to the multi-photon counting detector through free-space. In certain embodiments, the free-space light relay system includes a housing having a proximal end and a distal end, the proximal end being coupled to the multi-photon counting detector. The free-space relay system may include any combination of different optical adjustment components, such as one or more of lenses, mirrors, slits, pinholes, wavelength separators, or a combination thereof. For example, in some embodiments, free-space light relay systems of interest include one or more focusing lens. In other embodiments, the subject free-space light relay systems include one or more mirrors. In yet other embodiments, the free-space light relay system includes a collimating lens. In certain embodiments, suitable free-space light relay systems for propagating light to the multi-photon counting detector, but are not limited to, light relay systems such as those described in U.S. Pat. Nos. 7,643,142; 7,728,974 and 8,223,445, the disclosures of which is herein incorporated by reference.

Methods according to certain embodiments also include measuring light from the sample in the flow stream at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths. In some embodiments, methods include measuring the collected light over a range of wavelengths (e.g., 200 nm-1000 nm). For example, methods may include collecting spectra of light over one or more of the wavelength ranges of 200 nm-1000 nm. In yet other embodiments, methods include measuring collected light at one or more specific wavelengths. For example, the collected light may be measured at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, methods including measuring wavelengths of light which correspond to the fluorescence peak wavelength of certain fluorophores.

The collected light may be measured continuously or in discrete intervals. In some instances, methods include taking measurements of the light continuously. In other instances, the light is measured in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

Measurements of the collected light may be taken one or more times during the subject methods, such as 2 or more times, such as 3 or more times, such as 5 or more times and including 10 or more times. In certain embodiments, the light propagation is measured 2 or more times, with the data in certain instances being averaged.

As summarized above, methods include irradiating a sample in a flow stream (e.g., in a flow cytometer) with a light source. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Where methods include irradiating with a broadband light source, broadband light source protocols of interest may include, but are not limited to, a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, methods includes irradiating with a narrow band light source emitting a particular wavelength or a narrow range of wavelengths, such as for example with a light source which emits light in a narrow range of wavelengths like a range of 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Where methods include irradiating with a narrow band light source, narrow band light source protocols of interest may include, but are not limited to, a narrow wavelength LED, laser diode or a broadband light source coupled to one or more optical bandpass filters, diffraction gratings, monochromators or any combination thereof.

In certain embodiments, methods include irradiating the sample in the flow stream with one or more lasers. Lasers of interest may include pulsed lasers or continuous wave lasers. As discussed above, the type and number of lasers will vary depending on the sample as well as desired light collected and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the methods include irradiating the flow stream with a dye laser, such as a stilbene, coumarin or rhodamine laser. In yet other instances, methods include irradiating the sample in the flow stream with a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, methods include irradiating the sample in the flow stream with a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium$_2$O$_3$ laser or cerium doped lasers and combinations thereof.

The sample in the flow stream may be irradiated with one or more of the above mentioned light sources, such as 2 or more light sources, such as 3 or more light sources, such as 4 or more light sources, such as 5 or more light sources and including 10 or more light sources. The light source may include any combination of types of light sources. For example, in some embodiments, the methods include irradiating the sample in the flow stream with an array of lasers, such as an array having one or more gas lasers, one or more dye lasers and one or more solid-state lasers.

The sample in the flow stream may be irradiated with wavelengths ranging from 200 nm to 1500 nm, such as from 250 nm to 1250 nm, such as from 300 nm to 1000 nm, such as from 350 nm to 900 nm and including from 400 nm to 800 nm. For example, where the light source is a broadband light source, the sample may be irradiated with wavelengths from 200 nm to 900 nm. In other instances, where the light source includes a plurality of narrow band light sources, the sample may be irradiated with specific wavelengths in the range from 200 nm to 900 nm. For example, the light source may be plurality of narrow band LEDs (1 nm-25 nm) each independently emitting light having a range of wavelengths between 200 nm to 900 nm. In other embodiments, the narrow band light source includes one or more lasers (such as a laser array) and the sample is irradiated with specific wavelengths ranging from 200 nm to 700 nm, such as with a laser array having gas lasers, excimer lasers, dye lasers, metal vapor lasers and solid-state laser as described above.

Where more than one light source is employed, the sample in the flow stream may be irradiated with the light sources simultaneously or sequentially, or a combination thereof. For example, the sample in the flow stream may be simultaneously irradiated with each of the light sources. In other embodiments, the flow stream is sequentially irradiated with each of the light sources. Where more than one light source is employed to irradiate the sample sequentially, the time each light source irradiates the sample may independently be 0.001 microseconds or more, such as 0.01 microseconds or more, such as 0.1 microseconds or more, such as 1 microsecond or more, such as 5 microseconds or more, such as 10 microseconds or more, such as 30 microseconds or more and including 60 microseconds or more. For example, methods may include irradiating the sample with the light source (e.g. laser) for a duration which ranges from 0.001 microseconds to 100 microseconds, such as from 0.01 microseconds to 75 microseconds, such as from 0.1 microseconds to 50 microseconds, such as from 1 microsecond to 25 microseconds and including from 5 microseconds to 10 microseconds. In embodiments where sample in the flow stream is sequentially irradiated with two or more light sources, the duration sample is irradiated by each light source may be the same or different.

The time period between irradiation by each light source may also vary, as desired, being separated independently by a delay of 0.001 microseconds or more, such as 0.01 microseconds or more, such as 0.1 microseconds or more, such as 1 microsecond or more, such as 5 microseconds or more, such as by 10 microseconds or more, such as by 15 microseconds or more, such as by 30 microseconds or more and including by 60 microseconds or more. For example, the time period between irradiation by each light source may range from 0.001 microseconds to 60 microseconds, such as from 0.01 microseconds to 50 microseconds, such as from 0.1 microseconds to 35 microseconds, such as from 1 microsecond to 25 microseconds and including from 5 microseconds to 10 microseconds. In certain embodiments, the time period between irradiation by each light source is 10 microseconds. In embodiments where sample in the flow stream is sequentially irradiated by more than two (i.e., 3 or more) light sources, the delay between irradiation by each light source may be the same or different.

The sample in the flow stream may be irradiated continuously or in discrete intervals. In some instances, methods include irradiating the sample in the flow stream with the light source continuously. In other instances, the sample in the flow stream is irradiated with the light source in discrete intervals, such as irradiating every 0.001 millisecond, every 0.01 millisecond, every 0.1 millisecond, every 1 millisecond, every 10 milliseconds, every 100 milliseconds and including every 1000 milliseconds, or some other interval.

Depending on the light source, the sample in the flow stream may be irradiated from a distance which varies such as 0.01 mm or more, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more. Also, the angle or irradiation may also vary, ranging from 10° to 90°, such as from 15° to 85°, such as from 20° to 80°, such as from 25° to 75° and including from 30° to 60°, for example at a 90° angle.

The flow rate of the flow stream to detect light from the sample in the flow stream by multi-photon counting may vary, e.g., depending on the intensity of the light and may be 1 nL/min or more, such as 2 nL/min or more, such as 3 nL/min or more, such as 5 nL/min or more, such as 10 nL/min or more, such as 25 nL/min or more, such as 50 nL/min or more, such as 75 nL/min or more, such as 100 nL/min or more, such as 250 nL/min or more, such as 500 nL/min or more, such as 750 nL/min or more and including 1000 nL/min or more. In certain embodiments, the flow rate of the flow stream in the subject methods ranges from 1 nL/min to 500 nL/min, such as from 1 nL/min to 250 nL/min, such as from 1 nL/min to 100 nL/min, such as from 2 nL/min to 90 nL/min, such as from 3 nL/min to 80 nL/min, such as from 4 nL/min to 70 nL/min, such as from 5 nL/min to 60 nL/min and including rom 10 nL/min to 50 nL/min. In certain embodiments, the flow rate of the flow stream is from 5 nL/min to 6 nL/min.

The subject methods include detecting light from a sample in a flow stream (e.g., in a flow cytometer) by multi-photon counting. In some embodiments, the sample is a biological sample. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, or other biological liquid sample, e.g., tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

In certain embodiments, the biological sample contains cells. Cells that may be present in the sample include eukaryotic cells (e.g., mammalian cells) and/or prokaryotic cells (e.g., bacterial cells or archaeal cells). Samples may be obtained from an in vitro source (e.g., a suspension of cells from laboratory cells grown in culture) or from an in vivo source (e.g., a mammalian subject, a human subject, etc.). In some embodiments, the cellular sample is obtained from an in vitro source. In vitro sources include, but are not limited to, prokaryotic (e.g., bacterial, archaeal) cell cultures, environmental samples that contain prokaryotic and/or eukaryotic (e.g., mammalian, protest, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

Where the biological sample includes cells, methods of the present disclosure may include characterizing components of the cells, such as cell fragments, fragmented cell membranes, organelles, dead or lysed cells. In some embodiments, methods include characterizing the extracellular vesicles of the cells. Characterizing the extracellular vesicles of the cells may include identifying the type of extracellular vesicles in the cells or determining the size of the extracellular vesicles in the cells.

The data from the output signal (digital or analog output signal) may be recorded and analyzed in real time or stored in a data storage and analysis means, such as a computer, as desired. In embodiments of the present disclosure according to certain embodiments, components (e.g., extracellular vesicles) in the sample are detected and may be uniquely identified based on the measured light from each component in one or more detection channels, as desired. Light detected in detection channels used to identify the components may be measured following irradiation with the light source. Methods in certain embodiments also include data acquisition, analysis and recording, such as with a computer, where multiple data channels record multi-photon counting data from the sample as it passes through the detection region of the system. In these embodiments, analysis may include classifying and counting cells or components of cells (extracellular vesicles) such that each component is present as a set of digitized parameter values. The subject systems may be set to trigger on a selected parameter in order to distinguish the particles of interest from background and noise. "Trigger" refers to a preset threshold for detection of a parameter and may be used as a means for detecting passage of a component of interest through the detection region. Detection of an event that exceeds the threshold for the selected parameter triggers acquisition of multi-photon counting data for the sample component. Data is not acquired for components in the medium being assayed which cause a response below the threshold.

Multi-Photon Counting Light Detection Systems

Aspects of the present disclosure include light detection systems configured for detecting light from a sample in a flow stream (e.g., in a flow cytometer) by multi-photon counting. In embodiments, systems include a flow cell configured to propagate a sample in a flow stream, a light source for irradiating the sample in the flow stream, a detector and a photon counter that counts photons of the detected light by integrating photo-electron charge over a time interval. The detector may be any convenient detector, including for example a photomultiplier or a photodiode (e.g., an avalanche photodiode). In embodiments, the subject multi-photon counting detectors are characterized by a broadened range of light intensity detection and quantitation as compared to a single photon counting detection protocol, such as exhibiting a 2-fold or greater increase in the range of light intensity detection and quantitation, such as an increase by 3-fold or greater, such as by 5 fold or greater, such as by 10 fold or greater, such as by 25 fold or greater, such as by 50 fold or greater and including a 100-fold or greater increase in the range of light intensity detection and quantitation as compared to a single photon counting detection protocol.

In some embodiments, multi-photon counting detectors of interest include plurality of detectors. In some instances, the detectors are solid-state detectors, such as avalanche photodiodes. In certain instances, multi-photon counting detectors are configured as an array of photodetectors, such as an array of single-photon counting detectors. Where the multi-photon counting detector is an array of photodetectors, arrays of interest may include 3 photodetectors or more, such as 4 photodetectors or more, such as 5 photodetectors or more, such as 10 photodetectors or more, such as 25 photodetectors or more, such as 50 photodetectors or more, such as 75 photodetectors or more, such as 100 photodetectors or more, such as 250 photodetectors or more, such as 500 photodetectors or more, such as 750 photodetectors or more and including 1000 photodetectors or more. The photodetectors may be arranged in any geometric configuration as desired, where arrangements of interest include, but are not limited to a square configuration, rectangular configuration, trapezoidal configuration, triangular configuration, hexagonal configuration, heptagonal configuration, octagonal configuration, nonagonal configuration, decagonal configuration, dodecagonal configuration, circular configuration, oval configuration as well as irregular shaped configurations. The photodetectors in each photodetector array may be oriented with respect to the other (as referenced in an X-Z plane) at an angle ranging from 10° to 180°, such as from 15° to 170°, such as from 20° to 160°, such as from 25° to 150°, such as from 30° to 120° and including from 45° to 90°.

In certain embodiments, multi-photon counting detectors of interest include a silicon photomultiplier. Any convenient silicon photomultiplier may be employed as the multi-photon counting detector and may include a plurality of solid-state single photon counting detectors on a silicon substrate surface, such as a plurality of sequentially connected avalanche photodiodes on the surface of a silicon substrate. Each solid-state single photon counting detector (e.g., avalanche photodiode) on the silicon surface of silicon photomultipiers of interest may have an active surface with a width that ranges from 5 µm to 250 µm, such as from 10 µm to 225 µm, such as from 15 µm to 200 µm, such as from 20 µm to 175 µm, such as from 25 µm to 150 µm, such as from 30 µm to 125 µm and including from 50 µm to 100 µm and a length that ranges from 5 µm to 250 µm, such as from 10 µm to 225 µm, such as from 15 µm to 200 µm, such as from 20 µm to 175 µm, such as from 25 µm to 150 µm, such as from 30 µm to 125 µm and including from 50 µm to 100 µm, where the surface area of each solid-state detector (e.g., single-photon counting detectors such as an avalanche photodiode) on the silicon substrate surface ranges from 25 to µm$^2$ to 10000 µm$^2$, such as from 50 to µm$^2$ to 9000 µm$^2$, such as from 75 to µm$^2$ to 8000 µm$^2$, such as from 100 to µm$^2$ to 7000 µm$^2$, such as from 150 to µm$^2$ to 6000 µm$^2$ and including from 200 to µm$^2$ to 5000 µm$^2$. The number of solid-state detectors on the surface of the silicon substrate in silicon photomultipliers of interest may include 3 solid-state detectors or more, such as 4 solid-state detectors or more, such as 5 solid-state detectors or more, such as 10 solid-state detectors or more, such as 25 solid-state detectors or more, such as 50 solid-state detectors or more, such as 75 solid-state detectors or more, such as 100 solid-state detectors or more, such as 250 solid-state detectors or more, such as 500 solid-state detectors or more, such as 750 solid-state detectors or more and including 1000 solid-state detectors or more.

The size of the multi-photon counting photodetector array may vary depending on the amount of light from the sample in the flow stream being detected by multi-photon counting, the number of multi-photon counting photodetectors and the desired sensitivity and may have a length that ranges from 0.01 mm to 100 mm, such as from 0.05 mm to 90 mm, such as from 0.1 mm to 80 mm, such as from 0.5 mm to 70 mm, such as from 1 mm to 60 mm, such as from 2 mm to 50 mm, such as from 3 mm to 40 mm, such as from 4 mm to 30 mm and including from 5 mm to 25 mm. The width of the photodetector array may also vary, ranging from 0.01 mm to 100 mm, such as from 0.05 mm to 90 mm, such as from 0.1 mm to 80 mm, such as from 0.5 mm to 70 mm, such as from 1 mm to 60 mm, such as from 2 mm to 50 mm, such as from 3 mm to 40 mm, such as from 4 mm to 30 mm and including from 5 mm to 25 mm. As such, the active surface of the photodetector array may range from 0.1 mm$^2$ to 10000 mm$^2$, such as from 0.5 mm$^2$ to 5000 mm$^2$, such as from 1 mm$^2$ to 1000 mm$^2$, such as from 5 mm$^2$ to 500 mm$^2$, and including from 10 mm$^2$ to 100 mm$^2$.

In some embodiments, systems include photon counters that are configured to integrate photo-electron charge over a time interval. Time intervals according to the subject methods may be a duration that varies and may be 100 µs or less, such as 90 µs or less, such as 80 µs or less, such as 70 µs or less, such as 60 µs or less, such as 50 µs or less, such as 40 µs or less, such as 30 µs or less, such as 20 µs or less, such as 10 µs or less, such as 5 µs or less, such as 1 µs or less, such as 0.5 µs or less, such as 0.1 µs or less, such as 0.05 µs or less, such as 0.01 µs or less, such as 0.005 µs or less and including 0.001 µs or less. In some instances, time intervals for integrating photo-electron charge to count photons detected by the detector range from 0.001 µs to 100 µs, such as from 0.005 µs to 90 µs, such as from 0.01 µs to 80 µs, such as from 0.05 µs to 70 µs, such as from 0.1 µs to 60 µs and including from 0.5 µs to 50 µs.

In some instances, the photon counters are configured to count photons of the detected light by integrating photo-electron charge over a plurality of time intervals, such as over 2 time intervals or more, such as over 3 time intervals or more, such as over 4 time intervals or more, such as over 5 time intervals or more, such as over 10 time intervals or more, such as over 15 time intervals or more and including over 25 time intervals or more. Each of the plurality of time intervals for integrating photo-electron charge may independently be the same duration or a different duration. In some embodiments, two or more of the time intervals are the same duration and two or more of the time intervals are different durations.

Where the subject photon counters are configured to integrate photo-electron charge over a plurality of time intervals, each time interval may be separated by a reset period where no photons are counted (i.e., no integration of photo-electron charge from the detector). The reset period may be any duration, depending on the type of multi-photon counting detector (as described in greater detail below) and may be 0.0001 µs or more, such as 0.0005 µs or more, such as 0.001 µs or more, such as 0.005 µs or more, such as 0.01 µs or more, such as 0.05 µs or more, such as 0.1 µs or more, such as 0.5 µs or more, such as 1 µs or more, such as 2 µs or more, such as 3 µs or more, such as 5 µs or more, such as 10 µs or more, such as 25 µs or more, such as 50 µs or more, such as 100 µs or more, such as 250 µs or more, such as 500 µs or more and including a reset period of 1000 µs or more. For example, the duration of each reset period may independently range from 0.0001 µs to 1000 µs, such as from 0.001 µs to 750 µs, such as from 0.01 µs to 500 µs and including from 0.1 µs to 100 µs. Each reset period may be the same duration or a different duration. In some embodiments, two or more reset periods are the same duration and two or more reset periods are different durations.

FIG. 5 depicts a schematic of a detector setup according to certain embodiments. The detector (e.g., silicon photomultiplier, SiPM) detects light from the sample in the flow stream and outputs a waveform to an amplifier and photon counter and data processor. Each of the amplifier, photon counter and data processor are in communication with a controller computer which provides parameters for integration of the photo-electron charge as well as thresholds (described below) of light intensity to trigger photon counting.

In some embodiments, systems include a first photon counter that integrates photo-electron charge over a first time interval and a second photon counter that integrates photo-electron charge over a second time interval. In some instances, the first time interval and the second time interval partially overlap, such as overlapping for 0.0001 µs or more, such as 0.0005 µs or more, such as 0.001 µs or more, such as 0.005 µs or more, such as 0.01 µs or more, such as 0.05 µs or more, such as 0.1 µs or more, such as 0.5 µs or more including overlapping for 1 µs or more. In certain embodiments, systems include a first photon counter is configured to integrate photo-electron charge over a plurality of time intervals, each time interval being separated by a reset period and a second photon counter configured to integrate photo-electron charge during each reset period of the first photon counter. In some instances, the first photon counter is configured to integrate photo-electron charge during the reset period of the second photon counter. In these embodiments, the time interval for integration of photo-electron charge from the detected light by the second photon counter may overlap the time intervals of integration by the first photon counter, such as by 0.0001 µs or more, such as by 0.0005 µs or more, such as by 0.001 µs or more, such as by 0.005 µs or more, such as by 0.01 µs or more, such as by 0.05 µs or more, such as by 0.1 µs or more, such as by 0.5 µs or more including overlapping by 1 µs or more.

Figure 6:
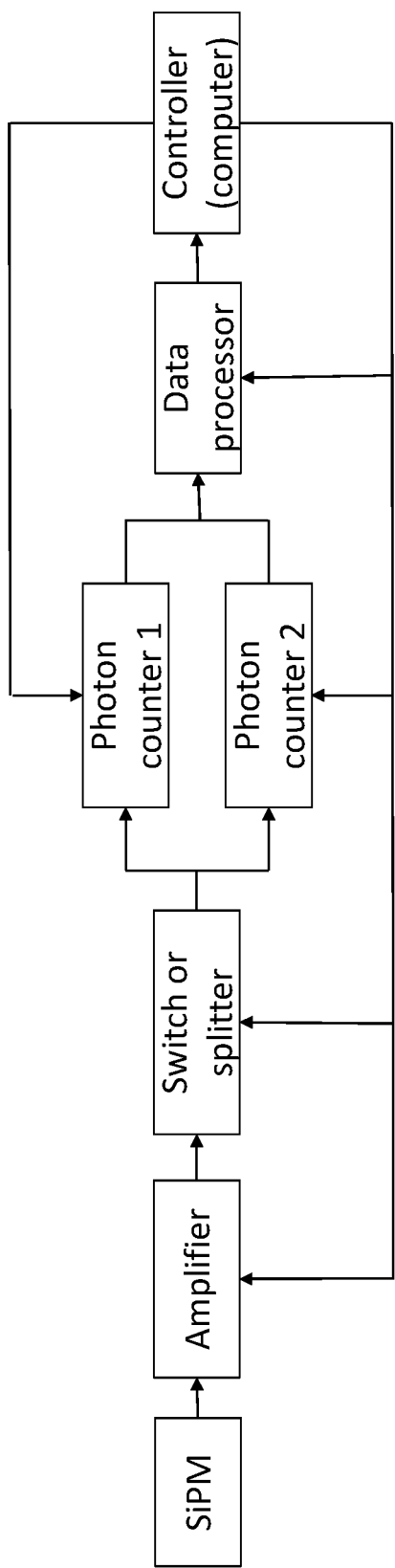
FIG. 6 depicts a schematic of a detector setup having two photon counters according to certain embodiments.

FIG. 6 depicts a schematic of a detector setup according to certain embodiments. The system in FIG. 6 includes a detector (e.g., a silicon photomultiplier, (SiPM)) that detects light from the sample in the flow stream and is in communication with an amplifier and a switch. The switch is coupled to two photon counters which integrate photo-electron charge for time intervals as described above, where the first photon counter is configured to integrate photo-electron charge during the reset period of the second photon counter and the second photon counter is configured to integrate photo-electron charge during the reset period of the first photon counter.

In still other embodiments, systems may include a photon counter that is configured to integrate photo-electron charge when the when light detected by the detector exceeds a predetermined threshold. For example, the subject systems may be configured to integrate photo-electron charge when the signal-to-noise ratio of the outputted waveform is 2:1 or more, such as a signal-to-noise ratio of 2.5:1, such as 3:1, such as 4:1, such as 5:1, such as 10:1 and including integrating photo-electron charge when the signal-to-noise ratio is 25:1. In embodiments, integration of the photo-electron charge is stopped when the detected light falls below the predetermined threshold. In these embodiments, the photon counters are configured with a time interval of integration that is dynamic and varies depending on the amount of light detected by the detector For example, the time intervals for integration of photo-electron charge by the subject photon counters may be 100 µs or less, such as 90 µs or less, such as 80 µs or less, such as 70 µs or less, such as 60 µs or less, such as 50 µs or less, such as 40 µs or less, such as 30 µs or less, such as 20 µs or less, such as 10 µs or less, such as 5 µs or less, such as 1 µs or less, such as 0.5 µs or less, such as 0.1 µs or less, such as 0.05 µs or less, such as 0.01 µs or less, such as 0.005 µs or less and including 0.001 µs or less. No predetermined time interval is programmed into the systems and the duration of integration of the photo-electron charge depends on the intensity of the signal from the detector.

In some embodiments, multi-photon counting detectors may be configured to generate a pulse from each photon that impinges onto the active surface of the photodetector, where multi-photon counting detectors of interest are configured to provide a count rate of 0.1 pulse counts per µsecond or more, such as 0.2 pulse counts per µsecond or more, such as 0.3 pulse counts per µsecond or more, such as 0.5 pulse counts per µsecond or more, such as 1 pulse count per µsecond or more, such as 2 pulse counts per µsecond or more, such as 3 pulse counts per µsecond or more, such as 5 pulse counts per µsecond or more, such as 10 pulse counts per µsecond or more, such as pulse counts per µsecond or more, such as 25 pulse counts per µsecond or more, such as 50 pulse counts per µsecond or more, such as 75 pulse counts per µsecond or more, such as 100 pulse counts per µsecond or more, such as 250 pulse counts per µsecond or more, such as 500 pulse counts per µsecond or more, such as 750 pulse counts per µsecond or more, such as 1000 pulse counts per µsecond or more and including 5000 pulse counts per µsecond or more. Accordingly, multi-photon counting detectors of interest are configured to provide a count rate of 0.1 photon counts per µsecond or more, such as 0.2 photon counts per µsecond or more, such as 0.5 photon counts per µsecond or more, such as 1 photon count per µsecond or more, such as 2 photon counts per µsecond or more, such as 3 photon counts per µsecond or more, such as 5 photon counts per µsecond or more, such as 10 photon counts per µsecond or more, such as 25 photon counts per µsecond or more, such as 50 photon counts per µsecond or more, such as 75 photon counts per µsecond or more, such as 100 photon counts per µsecond or more, such as 250 photon counts per µsecond or more, such as 500 photon counts per µsecond or more, such as 750 photon counts per µsecond or more, such as 1000 photon counts per µsecond or more and including 5000 photon counts per µsecond or more.

The subject multi-photon counting detectors (e.g., avalanche photodiode arrays) provide for high quantum efficiency in multi-photon counting, such as a quantum efficiency of 50% or more, such as 55% or more, such as 60% or more, such as 65% or more, such as 70% or more, such as 75% or more, such as 80% or more, such as 85% or more, such as 90% or more and including a quantum efficiency of 95% or more. In addition, multi-photon counting detectors for detecting light from a sample in a flow stream in the subject systems according to certain embodiments, exhibit a low dark count rate, such as a dark count rate of 100 counts per second or less, such as 90 counts per second or less, such as 75 counts per second or less, such as 50 counts per second or less, such as 40 counts per second or less, such as 30 counts per second or less, such as 25 counts per second or less, such as 20 counts per second or less, such as 15 counts per second or less, such as 10 counts per second or less, such as 5 counts per second or less, such as 4 counts per second or less, such as 3 counts per second or less, such as 2 counts per second or less and including a dark count rate of 1 count per second or less.

In embodiments, the multi-photon counting detector is configured to detect light from the sample in the flow stream by forward scattered light, side scattered light, transmitted light, emitted light (e.g., fluorescence or phosphorescence) or a combination thereof. In some embodiments, the multi-photon counting detector is configured to detect forward scattered light from the sample in the flow stream. In other embodiments, the multi-photon counting detector is configured to detect side scattered light from the sample in the flow stream. In yet other embodiments, the multi-photon counting detector is configured to detect light transmitted through the flow stream. In still other embodiments, the multi-photon counting detector is configured to detect emitted light (e.g., fluorescence or phosphorescence) from the sample in the flow stream.

Detectors of interest, in certain embodiments, include or are in electronic communication with a processor that outputs a signal in response to the detected light. In certain embodiments, the output signal is a digital output signal. In other embodiments, the output signal is an analog output signal. In some instances, the multi-photon counting detector is configured to output a digital output signal in response to the detected light. In other instances, the multi-photon counting detector is configured to output an analog output signal in response to the detected light. In still other instances, the multi-photon counting detector is configured to output a digital output signal and an analog output signal in response to the detected light. In yet other instances, the multi-photon counting detector is configured to simultaneously output a digital output signal and an analog output signal in response to the detected light. The detector may also provide a digital output signal in response to multi-photon counting of the light from the sample in the flow stream and provide an analog output signal in response to analog light detection of light from the sample in the flow stream. The type of output signal may be controlled by the user (e.g., the system user may manually or with assistance by a processor in a computer controlled system) where light detected may produce a digital output signal, analog output signal or a combination of both digital output signal and analog output signal. In other embodiments, systems are configured to automatically determine (i.e., without input or intervention by a user) a signal output. In one example, where light intensity from the sample in the flow stream is low, the system is configured to output a digital output signal in response to light detection (e.g., multi-photon counting). In another example, where light intensity from the sample in the flow stream is high, the system is configured to output an analog signal. In yet another example, the system is configured to automatically output (either sequentially or simultaneously, as desired) a digital output signal and an analog output signal.

In some embodiments, the type of output signal is determined (as set by a user or automatically determined without user input or intervention) by the type of light detected by the detector. In some instances, one or more of side scattered light, forward scattered light, emitted light is detected by both multi-photon counting to produce a digital output signal and by analog light detection to produce an analog output signal for the detected side scattered light, forward scattered light, emitted light or combination thereof. In one example, side scattered light from the sample in the flow stream is detected by multi-photon counting to produce a digital output signal and emitted light or forward scattered light from the sample in the flow stream is detected by analog light detection to produce an analog output signal. In another example, one or more of side scattered light and forward scattered light from the sample in the flow stream is detected by multi-photon counting to produce a digital output signal and emitted light is detected by analog light detection to produce an analog output signal.

The subject multi-photon counting detector may be in direct optical communication (i.e., through space) with the sample in the flow stream or may include one or more optical adjustment components positioned between the flow stream and the detector. The optical adjustment component is configured to change one or more properties of the light from the flow stream, such as the direction, intensity, the dimensions of the irradiation area and the alignment of the light propagated from the sample in the flow stream. Optical adjustment components may be any convenient device or structure which provides the desired change to the light beam and may include, but is not limited to, lenses, mirrors, beam splitters, collimating lenses, pinholes, slits, gratings, light refractors, and any combinations thereof. The subject multi-photon detector may include one or more optical adjustment components as needed, such as two or more, such as three or more, such as four or more and including five or more optical adjustment components.

In certain embodiments, systems further include an optical relay system, such as with fiber optics or a free space light relay system. In some embodiments, the optical relay system is a fiber optics light relay bundle and light is conveyed through the fiber optics light relay bundle to the multi-photon counting detector, as described above. In other embodiments, the optical relay system is a free-space light relay system. Free-space relay systems of interest may include any combination of different optical adjustment components, such as one or more of lenses, mirrors, slits, pinholes, wavelength separators, or a combination thereof, as described above.

In the subject systems, the optical adjustment component may be separate from the multi-photon detector (e.g., avalanche photodiode array), such as at a position between the flow stream and the detector or may be physically coupled to the multi-photon detector. In one example, the optical adjustment component is coupled to the multi-photon detector with a permanent or non-permanent adhesive or affixed with a fastener, such as a hook and loop fasteners, magnets, latches, screws, notches, countersinks, counter-bores, grooves, pins, tethers, hinges, Velcro or any combination thereof. In certain instances, the optical adjustment component is releasably attached. The term "releasably" is used herein in its conventional sense to mean that the optical adjustment component may be freely detached and re-attached from the multi-photon detector. In other instances, the optical adjustment component is co-molded to the multi-photon detector. In yet another example, the optical adjustment component is integrated directly into a device (e.g., a cartridge or cassette) containing the multi-photon detector.

Systems of interest for detecting light from a sample in a flow stream by multi-photon counting include a light source. In embodiments, the light source may be any suitable broadband or narrow band source of light. Depending on the components in the sample (e.g., cells, extracellular vesicles, beads, non-cellular particles, etc.), the light source may be configured to emit wavelengths of light that vary, ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a narrow band light source emitting a wavelength ranging from 200 nm to 900 nm. For example, the light source may be a narrow band LED (1 nm-25 nm) emitting light having a wavelength ranging between 200 nm to 900 nm. In some embodiments, the light source is a laser, such as continuous wave laser. For example, the laser may be a helium-neon (HeNe) laser. In certain embodiments, the light source is a laser in a flow cytometer. In other embodiments, the laser is a pulsed laser.

In other embodiments, the light source is a non-laser light source, such as a lamp, including but not limited to a halogen lamp, deuterium arc lamp, xenon arc lamp, a light-emitting diode, such as a broadband LED with continuous spectrum, superluminescent emitting diode, semiconductor light emitting diode, wide spectrum LED white light source, an multi-LED integrated. In some instances the non-laser light source is a stabilized fiber-coupled broadband light source, white light source, among other light sources or any combination thereof.

The light source may be positioned any suitable distance from the sample in the flow stream (e.g., in a flow cytometer), such as at a distance of 0.001 mm or more from the flow stream, such as 0.005 mm or more, such as 0.01 mm or more, such as 0.05 mm or more, such as 0.1 mm or more, such as 0.5 mm or more, such as 1 mm or more, such as 5 mm or more, such as 10 mm or more, such as 25 mm or more and including at a distance of 100 mm or. In addition, the light source irradiate the sample at any suitable angle (e.g., relative the vertical axis of the flow stream), such as at an angle ranging from 10° to 90°, such as from 15° to 85°, such as from 20° to 80°, such as from 25° to 75° and including from 30° to 60°, for example at a 90° angle.

The light source may be configured to irradiate the sample in the flow stream continuously or in discrete intervals. In some instances, systems include a light source that is configured to irradiate the sample in the flow stream continuously, such as with a continuous wave laser that continuously irradiates the sample in the flow stream at the interrogation point in a flow cytometer. In other instances, systems of interest include a light source that is configured to irradiate the sample at discrete intervals, such as every 0.001 milliseconds, every 0.01 milliseconds, every 0.1 milliseconds, every 1 millisecond, every 10 milliseconds, every 100 milliseconds and including every 1000 milliseconds, or some other interval. Where the light source is configured to irradiate the sample in the flow stream at discrete intervals, systems may include one or more additional components to provide for intermittent irradiation of the sample in the flow stream with the light source. For example, the subject systems in these embodiments may include one or more laser beam choppers, manually or computer controlled beam stops for blocking and exposing the sample to the light source.

In some embodiments, systems include a flow cell configured to propagate the sample in the flow stream. Any convenient flow cell which propagates a fluidic sample to a sample interrogation region may be employed, where in some embodiments, the flow cell includes a proximal cylindrical portion defining a longitudinal axis and a distal frustoconical portion which terminates in a flat surface having the orifice that is transverse to the longitudinal axis. The length of the proximal cylindrical portion (as measured along the longitudinal axis) may vary ranging from 1 mm to 15 mm, such as from 1.5 mm to 12.5 mm, such as from 2 mm to 10 mm, such as from 3 mm to 9 mm and including from 4 mm to 8 mm. The length of the distal frustoconical portion (as measured along the longitudinal axis) may also vary, ranging from 1 mm to 10 mm, such as from 2 mm to 9 mm, such as from 3 mm to 8 mm and including from 4 mm to 7 mm. The diameter of the of the flow cell nozzle chamber may vary, in some embodiments, ranging from 1 mm to 10 mm, such as from 2 mm to 9 mm, such as from 3 mm to 8 mm and including from 4 mm to 7 mm.

In certain instances, the flow cell does not include a cylindrical portion and the entire flow cell inner chamber is frustoconically shaped. In these embodiments, the length of the frustoconical inner chamber (as measured along the longitudinal axis transverse to the nozzle orifice), may range from 1 mm to 15 mm, such as from 1.5 mm to 12.5 mm, such as from 2 mm to 10 mm, such as from 3 mm to 9 mm and including from 4 mm to 8 mm. The diameter of the proximal portion of the frustoconical inner chamber may range from 1 mm to 10 mm, such as from 2 mm to 9 mm, such as from 3 mm to 8 mm and including from 4 mm to 7 mm.

In some embodiments, the sample flow stream emanates from an orifice at the distal end of the flow cell. Depending on the desired characteristics of the flow stream, the flow cell orifice may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In certain embodiments, flow cell of interest has a circular orifice. The size of the nozzle orifice may vary, in some embodiments ranging from 1 µm to 20000 µm, such as from 2 µm to 17500 µm, such as from 5 µm to 15000 µm, such as from 10 µm to 12500 µm, such as from 15 µm to 10000 µm, such as from 25 µm to 7500 µm, such as from 50 µm to 5000 µm, such as from 75 µm to 1000 µm, such as from 100 µm to 750 µm and including from 150 µm to 500 µm. In certain embodiments, the nozzle orifice is 100 µm.

In some embodiments, the flow cell includes a sample injection port configured to provide a sample to the flow cell. In embodiments, the sample injection system is configured to provide suitable flow of sample to the flow cell inner chamber. Depending on the desired characteristics of the flow stream, the rate of sample conveyed to the flow cell chamber by the sample injection port may be 1 µL/min or more, such as 2 µL/min or more, such as 3 µL/min or more, such as 5 µL/min or more, such as 10 µL/min or more, such as 15 µL/min or more, such as 25 µL/min or more, such as 50 µL/min or more and including 100 µL/min or more, where in some instances the rate of sample conveyed to the flow cell chamber by the sample injection port is 1 µL/sec or more, such as 2 µL/sec or more, such as 3 µL/sec or more, such as 5 µL/sec or more, such as 10 µL/sec or more, such as 15 µL/sec or more, such as 25 µL/sec or more, such as 50 µL/sec or more and including 100 µL/sec or more.

The sample injection port may be an orifice positioned in a wall of the inner chamber or may be a conduit positioned at the proximal end of the inner chamber. Where the sample injection port is an orifice positioned in a wall of the inner chamber, the sample injection port orifice may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion. In certain embodiments, the sample injection port has a circular orifice. The size of the sample injection port orifice may vary depending on shape, in certain instances, having an opening ranging from 0.1 mm to 5.0 mm, e.g., 0.2 to 3.0 mm, e.g., 0.5 mm to 2.5 mm, such as from 0.75 mm to 2.25 mm, such as from 1 mm to 2 mm and including from 1.25 mm to 1.75 mm, for example 1.5 mm.

In certain instances, the sample injection port is a conduit positioned at a proximal end of the flow cell inner chamber. For example, the sample injection port may be a conduit positioned to have the orifice of the sample injection port in line with the flow cell orifice. Where the sample injection port is a conduit positioned in line with the flow cell orifice, the cross-sectional shape of the sample injection tube may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. The orifice of the conduit may vary depending on shape, in certain instances, having an opening ranging from 0.1 mm to 5.0 mm, e.g., 0.2 to 3.0 mm, e.g., 0.5 mm to 2.5 mm, such as from 0.75 mm to 2.25 mm, such as from 1 mm to 2 mm and including from 1.25 mm to 1.75 mm, for example 1.5 mm. The shape of the tip of the sample injection port may be the same or different from the cross-section shape of the sample injection tube. For example, the orifice of the sample injection port may include a beveled tip having a bevel angle ranging from 1° to 10°, such as from 2° to 9°, such as from 3° to 8°, such as from 4° to 7° and including a bevel angle of 5°.

In some embodiments, the flow cell also includes a sheath fluid injection port configured to provide a sheath fluid to the flow cell. In embodiments, the sheath fluid injection system is configured to provide a flow of sheath fluid to the flow cell inner chamber, for example in conjunction with the sample to produce a laminated flow stream of sheath fluid surrounding the sample flow stream. Depending on the desired characteristics of the flow stream, the rate of sheath fluid conveyed to the flow cell chamber by the may be 25 µL/sec or more, such as 50 µL/sec or more, such as 75 µL/sec or more, such as 100 µL/sec or more, such as 250 µL/sec or more, such as 500 µL/sec or more, such as 750 µL/sec or more, such as 1000 µL/sec or more and including 2500 µL/sec or more.

In some embodiments, the sheath fluid injection port is an orifice positioned in a wall of the inner chamber. The sheath fluid injection port orifice may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. The size of the sample injection port orifice may vary depending on shape, in certain instances, having an opening ranging from 0.1 mm to 5.0 mm, e.g., 0.2 to 3.0 mm, e.g., 0.5 mm to 2.5 mm, such as from 0.75 mm to 2.25 mm, such as from 1 mm to 2 mm and including from 1.25 mm to 1.75 mm, for example 1.5 mm.

In some embodiments, systems further include a pump in fluid communication with the flow cell to propagate the flow stream through the flow cell. Any convenient fluid pump protocol may be employed to control the flow of the flow stream through the flow cell. In certain instances, systems include a peristaltic pump, such as a peristaltic pump having a pulse damper. The pump in the subject systems is configured to convey fluid through the flow cell at a rate suitable for multi-photon counting of light from the sample in the flow stream. In some instances, the rate of sample flow in the flow cell is 1 nL/min or more, such as 2 nL/min or more, such as 3 nL/min or more, such as 5 nL/min or more, such as 10 nL/min or more, such as 25 nL/min or more, such as 50 nL/min or more, such as 75 nL/min or more, such as 100 nL/min or more, such as 250 nL/min or more, such as 500 nL/min or more, such as 750 nL/min or more and including 1000 nL/min or more. For example, the system may include a pump that is configured to flow sample through the flow cell at a rate that ranges from 1 nL/min to 500 nL/min, such as from 1 nL/min to 250 nL/min, such as from 1 nL/min to 100 nL/min, such as from 2 nL/min to 90 nL/min, such as from 3 nL/min to 80 nL/min, such as from 4 nL/min to 70 nL/min, such as from 5 nL/min to 60 nL/min and including rom 10 nL/min to 50 nL/min. In certain embodiments, the flow rate of the flow stream is from 5 nL/min to 6 nL/min.

In certain embodiments, the subject systems are flow cytometric systems employing the above described multi-photon counting detectors for detecting light from a sample in a flow stream by multi-photon counting. Suitable flow cytometry systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem. January;* 49(pt 1):17-28; Linden, et. al., *Semin Throm Hemost.* 2004 October; 30(5):502-11; Alison, et al. *J Pathol,* 2010 December; 222(4):335-344; and Herbig, et al. (2007) *Crit Rev Ther Drug Carrier Syst.* 24(3):203-255; the disclosures of which are incorporated herein by reference. In certain instances, flow cytometry systems of interest include BD Biosciences FACSCanto™ flow cytometer, BD Biosciences FACSVantage™, BD Biosciences FACSort™, BD Biosciences FACSCount™, BD Biosciences FACSscan™, and BD Biosciences FACSCalibur™ systems, a BD Biosciences Influx™ cell sorter, BD Biosciences Jazz™ cell sorter and BD Biosciences Aria™ cell sorter or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300;

8,233,146; 8,753,573; 8,975,595; 9,092,034; 9,095,494 and 9,097,640; the disclosures of which are herein incorporated by reference.

Computer-Controlled Systems

Aspects of the present disclosure further include computer controlled systems for practicing the subject methods, where the systems further include one or more computers for complete automation or partial automation of a system for practicing methods described herein. In some embodiments, systems include a computer having a computer readable storage medium with a computer program stored thereon, where the computer program when loaded on the computer includes instructions for irradiating a sample in a flow stream with a light source as described above, algorithm for detecting light from the sample in the flow stream with a multi-photon counting detector and algorithm for counting photons of the detected light by integrating photo-electron charge over a time interval.

In embodiments, the system includes an input module, a processing module and an output module. In some embodiments, the subject systems may include an input module such that parameters or information about each fluidic sample, intensity and wavelengths (discrete or ranges) of the applied light source, flow cell diameter, number of light channels, number of detection regions, duration of irradiation by the light source, number of different light sources, distance from light source to the flow channel, focal length of any optical adjustment components, refractive index of flow channel medium (e.g., sheath fluid), presence of any wavelength separators, properties of wavelength separators including bandpass width, opacity, grating spacing as well as properties and sensitivity of multi-photon counting photodetectors including thresholds for light intensity to trigger integration of photo-electron charge as well as predetermined time intervals for photon counting.

The processing module includes memory having a plurality of instructions for performing the steps of the subject methods, such as irradiating the sample in the flow stream; and detecting one or more wavelengths of light from the sample by multi-photon counting as described above.

After the processing module has performed one or more of the steps of the subject methods, an output module communicates the results to the user, such as by displaying on a monitor or by printing a report.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for performing the steps of the subject methods, such as irradiating a sample in a flow stream with a light source and detecting light from the sample in the flow stream with the multi-photon counting detector and counting photons of the detected light by integrating photo-electron charge over a time interval.

The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the subject systems and other external devices such as a computer terminal (for example, at a physician's office or in hospital environment) that is configured for similar complementary data communication.

In one embodiment, the communication interface is configured for infrared communication, Bluetooth® communication, or any other suitable wireless communication protocol to enable the subject systems to communicate with other devices such as computer terminals and/or networks, communication enabled mobile telephones, personal digital assistants, or any other communication devices which the user may use in conjunction therewith, in managing the treatment of a health condition, such as HIV, AIDS or anemia.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the subject systems are configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen.

In some embodiments, the communication interface is configured to automatically or semi-automatically communicate data stored in the subject systems, e.g., in an optional data storage unit, with a network or server device using one or more of the communication protocols and/or mechanisms described above.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Windows 8, iOS, Sun Solaris, Linux, OS/400, Compaq Tru64 Unix, SGI IRIX, Siemens Reliant Unix, and others.

Kits

Aspects of the invention further include kits, where kits include a flow cell configured to propagate a sample in a flow stream, a detector (e.g., a silicon photomultiplier, (SiPM)), a photon counter that counts photons of the detected light by integrating photo-electron charge over a time interval and an optical adjustment component as described herein. In some embodiments, kits further include one or more excitation sources, such as a laser or an LED. In certain instances, kits can include one or more assay components (e.g., labeled reagents, buffers, etc., such as described above). In some instances, the kits may further include a sample collection device, e.g., a lance or needle configured to prick skin to obtain a whole blood sample, a pipette, etc., as desired. The subject kits may also include a waste collection container.

In some embodiments, kits include a fluidic composition, such as a digestive enzyme composition or buffer solution. Example buffers may include but are not limited to PBS (phosphate) buffer, acetate buffer, N,N-bis(2-hydroxyethyl) glycine (Bicine) buffer, 3-{[tris(hydroxymethyl)methyl] amino}propanesulfonic acid (TAPS) buffer, 2-(N-morpholino)ethanesulfonic acid (MES) buffer, citrate buffer, tris(hydroxymethyl)methylamine (Tris) buffer, N-tris(hydroxymethyl)methylglycine (Tricine) buffer, 3-[N-Tris(hydroxymethyl)methylamino]-2-hydroxypropanesulfonic Acid (TAPSO) buffer, 4-2-hydroxyethyl-1-piperazineethanesulfonic acid (HEPES) buffer, 2-{[tris(hydroxymethyl)methyl]amino}ethanesulfonic acid (TES) buffer, piperazine-N,N'-bis(2-ethanesulfonic acid) (PIPES) buffer, dimethylarsinic acid (Cacodylate) buffer, saline sodium citrate (SSC) buffer, 2(R)-2-(methylamino)succinic acid (succinic acid) buffer, potassium phosphate buffer, N-Cyclohexyl-2-aminoethanesulfonic acid (CHES) buffer, among other types of buffered solutions. In certain instances, the fluidic composition is a cytometer-grade solution.

In still other embodiments, kits include a labelling reagent composition. For example, the labelling reagent composition may be a fluorophore, chromophore, enzyme, redox label, radiolabels, acoustic label, Raman (SERS) tag, mass tag, isotope tag, magnetic particle, microparticle or nanoparticle or a combination thereof. In some cases, the labelling reagent includes a labelled biomolecule, such as a polypeptide, a nucleic acid and a polysaccharide that is labelled with a fluorophore, chromophore, enzyme, redox label, radiolabels, acoustic label, Raman (SERS) tag, mass tag, isotope tag, magnetic particle, microparticle or nanoparticle or a combination thereof.

The various assay components of the kits may be present in separate containers, or some or all of them may be pre-combined. For example, in some instances, one or more components of the kit, e.g., each multi-photon counting detector is present in a sealed pouch, e.g., a sterile foil pouch or envelope.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

The subject multi-photon counting light detection systems, methods and computer systems find use in a variety of applications where it is desirable to analyze and sort particle components in a sample in a fluid medium, such as a biological sample. Embodiments of the invention find use where it is desirable to provide an improved cell sorting accuracy and enhanced sub-particle detection.

Embodiments of the invention also find use in applications where cells prepared from a biological sample may be desired for research, laboratory testing or for use in therapy. In some embodiments, the subject methods and devices may facilitate obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems may facilitate obtaining cells from fluidic or tissue samples to be used in therapy. Methods and devices of the present disclosure allow for detecting and collecting cells from a biological sample (e.g., organ, tissue, tissue fragment, fluid) with enhanced efficiency and low cost as compared to traditional flow cytometry systems.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:
   irradiating a sample in a flow stream with a light source;
   detecting light from the sample in the flow stream with a multi-photon counting detector;
   generating a plurality of data signals from the detected light; integrating photo-electron charge of the plurality of data signals over a time interval; and
   counting photons of the detected light with one or more photon counters based on the integrated photo-electron charge over the time interval,
   wherein counting photons comprises: integrating photo-electron charge with a first photon counter over a plurality of time intervals, each time interval separated by a reset period therebetween; and integrating photo-electron charge with a second photon counter during each reset period of the first photon counter.

2. The method according to claim 1, wherein counting photons comprises integrating photo-electron charge over a plurality of time intervals.

3. The method according to claim 2, wherein counting photons comprises a reset period between each of the time intervals.

4. The method according to claim 2, wherein two or more of the time intervals overlap.

5. The method according to claim 2, wherein each time interval is the same.

6. The method according to claim 2, wherein each time interval is different.

7. The method according to claim 2, wherein two or more of the time intervals are the same and two or more of the time intervals are different.

8. The method according to claim 2, wherein counting photons comprises:
   integrating photo-electron charge with a first photon counter over a first time interval; and integrating photo-electron charge with a second photon counter over a second time interval.

9. The method according to claim 8, wherein the first time interval and the second time interval at least partially overlap.

10. The method according to claim 1, wherein counting photons comprises integrating photo-electron charge when the detected light exceeds a predetermined threshold.

11. The method according to claim 10, wherein counting photons comprises stopping integration of photo-electron charge when the number of photons detected light falls below the predetermined threshold.

12. The method according to claim 1 wherein counting photons comprises counting a plurality of pulses, wherein each pulse is produced by a single photon.

13. The method according to claim 12, wherein light intensity from the sample in the flow stream is determined by the number of counted pulses.

14. The method according to claim 1, further comprising measuring the detected light at one or more wavelengths.

15. The method according to claim 1, wherein the detected light is forward scattered light, side scattered light, transmitted light, emitted light or a combination thereof.

16. The method according to claim 15, wherein the detected light is side scattered light.

17. The method according to claim 1, wherein the light is detected by a detector array comprising a plurality of detectors.

18. The method according to claim 17, wherein the detector array comprises a plurality of solid-state detectors.

19. The method according to claim 18, wherein the solid-state detectors are avalanche photodiodes.

* * * * *